US006372219B1

(12) United States Patent
Salafsky et al.

(10) Patent No.: US 6,372,219 B1
(45) Date of Patent: Apr. 16, 2002

(54) PARASITE-DERIVED ANTI-INFLAMMATORY IMMUNOMODULATORY PROTEIN

(76) Inventors: Bernard Salafsky, 5730 Clarendon Dr., Rockford, IL (US) 61114; Ramaswamy Kalyanasundaram, 1423 Illini Dr., Rockford, IL (US) 61107; Takeshi Shibuya, 2-14-19 Kamiohsaki, Shinagawa-Ku Tokyo (JP)

( * ) Notice: Subject to any disclaimer, the term of this patent is extended or adjusted under 35 U.S.C. 154(b) by 0 days.

(21) Appl. No.: 09/180,446

(22) PCT Filed: Mar. 14, 1997

(86) PCT No.: PCT/US97/03953

§ 371 Date: Oct. 19, 1999

§ 102(e) Date: Oct. 19, 1999

(87) PCT Pub. No.: WO97/33613

PCT Pub. Date: Sep. 18, 1997

Related U.S. Application Data

(60) Provisional application No. 60/013,423, filed on Mar. 14, 1996.

(51) Int. Cl.[7] .......................... A61K 39/00; C12P 21/06; C12N 15/09; C07K 1/00
(52) U.S. Cl. .................. 424/184.1; 424/9.1; 424/265.1; 435/69.1; 435/69.3; 530/350; 530/395
(58) Field of Search ............................ 424/184.1, 265.1, 424/9.1; 435/69.1, 69.3; 530/350, 395

(56) References Cited

FOREIGN PATENT DOCUMENTS

FR           86 11986    *  8/1986   ........... C07K/13/00

OTHER PUBLICATIONS

Houghten et al. Vaccines, 1986, Edited by Fred Brown: Cold Spring Harbor Laboratory, 1990.*

Bowie et al. Science, vol. 247: 1990; p. 1306; p. 1308, 1986.*

Ramaswamy et al, Immunology and Infectious diseases, vol. 5, 100–107, 1995.*

John A.Smith, Short Protocols In Molecular Biology:Edited by Frid Ausubel ( Chapter 10, pp. 10–33 to 10–34), 1992.*

Ramaswamy et al, Journal of Inflammation 46:13–22, 1996.*

Benjamini and Leskowitz, Immunology A Short Course: WILEY–LISS, A John Wiley &Sons, Inc,Publication, Newyork), 1991.*

* cited by examiner

*Primary Examiner*—Lynette R. F. Smith
*Assistant Examiner*—Padma Baskar
(74) *Attorney, Agent, or Firm*—Marshall, Gerstein, & Borun

(57) ABSTRACT

A protein with anti-inflammatory, and immunomodulatory functions was identified and isolated from the excretory/secretions of a human parasite *Schistosoma mansoni*. This protein, designated herein as Sm 16.8, is released by schistosomes upon entry into human skin. Under in vitro conditions Sm 16.8 is shown to stimulate the production of anti-inflammatory cytokine Interleukin-1 receptor antagonist (IL-1ra) in human keratinocytes and transcriptionally down regulate the production of proinflammatory cytokines IL-1 α and IL-1 β.

2 Claims, No Drawings

PARASITE-DERIVED ANTI-INFLAMMATORY IMMUNOMODULATORY PROTEIN

This application claims priority from U.S. provisional application No. 60/013,423 filed on Mar. 14, 1996.

BACKGROUND OF THE INVENTION

In one of its life-stages the parasite *Schistosoma mansoni* (*S. mansoni*), which causes the tropical disease schistosomiasis, has the unique ability to penetrate intact, unabraded human skin. After gaining entry into the host, the parasite spends over 48 hrs in various layers of the skin without eliciting any marked tissue response. This subdued inflammatory response is largely responsible for the parasite's ability to pass through the skin virtually undetected by its human host.

Other schistosomes such as *Trichobilharia oceltata* (a bird parasite) which also can penetrate intact human skin, causes a severe inflammatory response in the skin (commonly called swimmer's itch) which results in the parasite's elimination from the host. Therefore, suppression of inflammatory responses in the skin appears to be crucial for the survival of schistosomes in its human host. Because *Schistosoma mansoni* does not elicit such a response, it would be useful to determine the mechanisms by which the inflammatory response is reduced or suppressed and to exploit such mechanisms as anti-inflammatory therapeutics for treating any inflammatory condition.

SUMMARY OF THE INVENTION

The present invention is directed to an isolated purified polypeptide designated Sm 16.8 or variants, fragments, derivatives, homologs or analogs thereof. The variants, fragments, derivatives, homologs or analogs may have a biological activity of Sm 16.8 and/or be immunologically active, that is, capable of inducing antibody formation, the antibodies being directed to one or more epitopes of the Sm 16.8 polypeptide.

Antibodies that specifically bind to polypeptides of the present invention are also within the scope of the present invention. Such antibodies may serve as therapeutics and/or diagnostic products. The antibodies may be polyclonal or monoclonal.

More particularly, the invention is directed to a polypeptide having a molecular weight of 16.8 kDa on a non-reducing SDS-polyacrylamide gel and has an isoelectric point of 5.9. The polypeptide of the present invention is obtainable from the parasite *Schistosoma mansoni* and may be a secretion/excretion product of the schistosome.

Also, comprehended by the invention are DNAs encoding the polypeptides of the present invention as well as vectors comprising the DNAs of the invention, host cells transformed with the vector and expression products derived therefrom. Host cells may be procaryotic or eucaryotic host cells.

The invention is also directed to vaccines comprising one or more polypeptides according to the present invention which may also include suitable adjuvants, diluents or carrier substances, the vaccines being useful for immunoprophylaxis of schistosomiasis.

Pharmaceutical compositions comprising Sm 16.8 variants, fragments, derivatives, homologs or analogs of the polypeptide in combination with pharmaceutically acceptable diluents, adjuvants and carriers are also contemplated by the present invention.

The invention is further directed to methods of suppressing or preventing inflammation by administering to a subject an anti-inflammatory dose of a polypeptide or pharmaceutical compositions according to the present invention.

Methods for treating inflammation associated diseases such as cutaneous disease are also within the scope of the invention. Such methods comprise administering to a subject a therapeutically effective dose of a polypeptide or pharmaceutical composition according to the present invention. The polypeptides may be administered topically, for example, in a suitable cream, lotion or salve that may include excipients useful in transporting the biologically active polypeptides into the skin.

Methods for treating systemic diseases characterized by inflammatory processes, using the polypeptides of the invention are also contemplated by the present invention. Such diseases may be autoimmune diseases.

DETAILED DESCRIPTION OF THE INVENTION

During penetration into the skin, parasites such as those of the species *Schistosoma* continuously excrete/secrete substances (ES) into their surroundings in order to aid their passage and/or as part of their metabolism.

These ES products are known to contain different types of proteins and lipids, many of whose function are not fully known. By culturing these parasites (i.e., schistosomes) in vitro ES products have been collected, purified and analyzed for their functional capabilities. One of the major components of the ES products are proteins. Given that *S. mansoni* and *T. ocellata* differ in their ability to induce inflammation in the skin, the proteins in the ES products of the two parasites were analyzed in an attempt to identify whether ES products of *S. mansoni* contain any factors that have the capacity to modulate inflammatory responses in human skin that are not contained in the ES products of *T. ocellata*. These studies revealed the presence of a protein in the secretions of *S. mansoni* but not *T. oceltata*, that has the ability to suppress inflammation.

Cytokines, natural hormone like substances produced by many cells in the skin, may play a central role in initiating, promoting or suppressing inflammation. Cytokines such as Interleukin-1α(IL-1α) and IL-1β promote inflammation, whereas, cytokines such as IL-1ra suppress inflammation. In the skin, cells such as keratinocytes, Langerhans cells, lymphocytes or mast cells can produce an array of pro-inflammatory cytokines upon activation. Yet, penetration and migration of *S. mansoni* through the skin fails to induce any inflammatory, response.

Keratinocytes constitute over 95% of the cells in human skin. It has been shown repeatedly that depending upon the stimulus, human keratinocytes may produce the pro-inflammatory cytokine IL-1α or the anti-inflammatory cytokine IL-1ra. Production of large quantities of IL-1ra locally results in the suppression of inflammatory responses.

The immunological basis for many cutaneous diseases such as atopic dernatitis, urticaria, contact sensitivity, cutaneous allergic conditions and psoriasis, is the accumulation of inflammatory cells in the epidermis and dermis. Any drug that can reduce or suppress accumulation of inflammatory cells in the skin will alleviate the clinical symptoms associated with these diseases.

Other inflammatory diseases are associated with the inflammatory processes in other organs of the body and are likewise susceptible to treatment with certain anti-inflammatory drugs.

A *Schistosoma mansoni* derived protein, Sm 16.8, that selectively up regulates IL-1ra production in human keratinocytes was identified and characterized. When added to human keratinocyte cultures at a concentration of 5 µg/1× $10^5$ cells, Sm 16.8 stimulated the production of IL-1ra within 4 hrs. Intracellular message (mRNA) for IL-1ra in these cells increased from 4 hrs after treatment and attained maximum values within 8 hrs. Statistically significant amounts of IL-1ra were also found intracellularly and in the culture supernatants of human keratinocytes after treatment with Sm 16.8. IL-1ra is a natural antagonist of IL-1, in that it competes with IL-1α and IL-1β for the IL-1 receptor. Binding of IL-1α or IL-1β to IL-1 receptors expressed on many cells results in a cascade of events leading to inflammation. However, binding of IL-1ra to IL-1 receptors fails to induce any receptor mediated responses. Therefore, occupancy of all available IL-1 receptors by IL-1ra results in the blocking of all IL-1 mediated responses. Since, IL-1ra binds to IL-1 receptors with affinity equal to or higher than those of IL-1α or IL-1β and, since the dissociation rate constant of IL-1ra from IL-1 receptors is several-fold lower than that for IL-1α and IL-1β, a higher concentration of IL-1ra in the local microenvironment can effectively block all the IL-1 mediated responses including inflammation. Given evidence that Sm 16.8 can stimulate a 100–400 fold increase in IL-1ra production from human keratinocytes, which are the major cell type in the skin, the use of Sm 16.8 as an anti-inflammatory substance against inflammatory diseases including inflammatory conditions in human skin is within the scope of the present invention.

In addition to its effect in stimulating IL-1ra production, Sm 16.8 suppresses IL-1α and IL-1β synthesis in human keratinocytes both at the transcriptional and translational levels. When added to human keratinocyte cultures that were stimulated with lipopolysaccharide—a bacterial envelope protein that induces marked IL-1α production in human keratinocytes, the parasite-derived protein suppressed IL-1α production by keratinocytes in a dose dependent fashion. At a concentration of 5 µg/ml per 1×$10^5$ cells, Sm 16.8 completely inhibited IL-1α, and IL-1β RNA production in human keratinocytes. Thus, Sm 16.8 appears to act by providing a two-pronged approach towards reducing inflammation, (i) by stimulating the production of IL-1ra in human skin cells and (ii) by transcriptionally down regulating the production of the pro-inflammatory cytokines IL-1α and IL-1β.

Lymphocytes collected from infected animals often respond to recall antigens (antigens to which an animal has been previously exposed) by rapid multiplication (lymphoproliferation) and by secreting cytokines, specifically IL-2. This immunological phenomenon provides the basis of many vaccination protocols. It is clearly shown herein that lymphocytes recovered from the spleen and axillary lymphnodes of *S. mansoni* infected mice exhibit recall response to parasite Schistosoma antigens. However, when Sm 16.8 is present in the antigen mixture, the lymphocytes are unable to respond to the antigens. Once the antigen mixture is depleted of Sm 16.8 the recall response is regained. When Sm 16.8 is then added back to the depleted antigen mixture, ability of the lymphocytes to respond to the recall antigens is again lost. This demonstrates that the anti-inflammatory protein Sm 16.8 also has immunomodulatory functions.

Success of a vaccination protocol largely depends on the initiation of an appropriate immune response at the site of vaccination. In mice a radiation-attenuated vaccine [Richter et al., *Parasitology Today*, 11:288–293 (1995)] has been shown to confer protection against *S. mansoni* infection. Such vaccination results in an initial interferon-γ (IFN-γ) response in the skin and axillary lymph nodes. Whereas, a normal infection results in an initial IL-4 and IL-10 but no IFN-γ response. Thus, development of an early IFN-γ response in the skin and its associated axillary lymph nodes is correlated with protection. In vitro studies show that Sm 16.8 suppresses IFN-γ response in axillary lymph node cells stimulated with recall antigens. Therefore, it is possible that Sm 16.8 may also interfere with other aspects of the development of immune response against the parasite.

In an important aspect of the invention, antagonists of Sm 16.8 activity such as peptides (the preparation of which are discussed below) and antibodies are produced which, upon challenge with *S. mansoni*, will block the anti-inflammatory activity/or immunomodulatory effects of Sm 16.8. Antibodies are produced by immunization of a host animal with polypeptides according to the present invention using methods well known in the art.

Another anti-inflammatory protein designated Transthyretin (TTR) [Borish et al., *Inflammation*, 16(5):471–484 (1992)], has a molecular mass close to the parasite-derived protein Sm 16.8 of the present invention. TTR has a molecular mass of 17 kDa and is produced by human liver cells. However, studies show that TTR is different from Sm 16.8 both in its physical property and function. TTR was originally purified from human serum by an anion exchange chromatography, molecular sieve HPLC and hydroxyl apatite chromatography suggesting that TTR is a basic protein. Whereas Sm 16.8 is an acidic protein with a pI of 5.8. [See, e.g., Borish et al., *Inflamination*, 16(5):471–484 (1992); and Zocchi et al., *Immunol. Letters*, 13(5):245–253 (1986).]

The anti-inflammatory activity of TTR depends on its ability to inhibit secretion of IL-1α and IL-1β from endothelial cells and monocytes similar to Sm 16.8. However, TTR does not inhibit the intracellular synthesis of IL-1 as does Sm 16.8, rather TTR increases the level of IL-1 mRNA and IL-1 protein concentration intracellularly. This means the TTR treated cells are continually synthesizing the pro-inflammatory cytokine IL-1 in their cytoplasm but are unable to secrete the cytokine, whereas, in Sm 16.8 treated cells the synthesis of pro-inflammatory cytokines IL-1α and IL-1β is completely inhibited. In addition, unlike TTR, Sm 16.8 is shown to stimulate the production and secretion of significant quantities of the anti-inflammatory cytokine IL-1ra. Thus overall, the function of Sm 16.8 provides advantages in reducing an inflammatory response in the skin not obtainable with TTR because it reduces or eliminates the pro-inflammatory cytokines present in the microenvironment of the tissue.

Having isolated and purified Sm 16.8 its amino acid composition and its N-terminal amino acid sequence are obtainable using routine methodologies well known to those of ordinary skill in the art. Knowledge of the N-terminal amino acid sequence of Sm 16.8 enables a person of ordinary skill in the art to obtain the DNA encoding the protein by synthesizing appropriate polynucleotide probes or primers based on the determined amino acid sequence and by using the polynucleotides or probes to screen genomic DNA libraries or cDNA libraries obtainable from *S. mansoni* by hybridization methods, or by use of methods such as the polymerase chain reaction (PCR). Upon isolating and determining the sequence of a DNA encoding Sm 16.8, a person of ordinary skill in the art having knowledge of the genetic code would be readily able to deduce the complete amino acid sequence of Sm 16.8. Vectors comprising a DNA according to the present invention (e.g., plasmids, viruses, bacteriophage, cosmids and others) are useful for expressing the Sm 16.8 DNA in host cells. Host cells may be eucaryotic or procaryotic cells. Such cells include yeast cells and bacterial cells such as *E. coli* and others. Host cells expressing DNAs of the present invention provide an abundant reproducible source of Sm 16.8 for use in the practice of the invention.

DNA of the present invention are also useful for preparing muteins, variants or analogs of Sm 16.8, having amino acid substitutions at specified sites in the protein and which retain a biological activity of Sm 16.8. Methods for selecting candidate amino acids for substitution are well known in the art. [See, e.g., Kyte et al., *J. Mol. Biol.*, 157:105–132 (1982).] The DNA may also be used to prepare truncations or fragments of Sm 16.8 and to prepare derivatives of Sm 16.8 such as Sm 16.8 fusion proteins. Exemplary proteins for fusion to Sm 16.8 include β-galactosidase, glutathione-S-transferase, (His-tags) and others well known in the art. The fusion may be made at the N-terminus, carboxyl terminus of the polypeptide or may be inserted at an internal site of the protein. Such fusion proteins may be useful in preparing vaccines for enhancing the immune response directed to Sm 16.8 and thereby serving as an immunoprophylactic against infection with *S. mansoni*. The vaccine may also comprise suitable diluents, adjuvants, and carriers.

Useful fragments of Sm 16.8 may also be prepared by the proteolytic digestion of the purified protein with one or more of a variety of well known proteolytic reagents such as cyanogen bromide and/or proteolytic enzymes such as the carboxypeptidases, asparaginases and others well known in the art.

DNAs, according to the present invention, may also be used to isolate DNA homologous from other species by hybridization at high stringency or by PCR under stringent conditions. Molecular techniques for accomplishing the foregoing are well known and described in detail in numerous publications including Ausubel et al., *Current Protocols in Molecular Biology*, John Wiley and Sons (1996), which is incorporated herein by reference.

Polypeptides of the present invention may also be covalently modified by the addition of chemical moieties. Exemplary chemical moieties include polyethylene glycol.

Once the primary amino acid composition of the protein is obtained the three-dimensional structure of the protein is determined, e.g., by crystallization and x-ray diffraction, and the active binding sites could be identified for specific therapeutic applications or immunomodulation. [See generally, e.g., PCT/U.S. Ser. No. 93/05548 published Dec. 23, 1993.] Such therapeutics may be small peptides or polypeptide fragments that bind to the active site thereby blocking its activity or may be other small molecules which interfere with the active site of the polypeptide.

EXAMPLE 1

Isolation and Purification of Sm 16.8

*Biomphalaia glabrata* species of snails infected with *S. mansoni* were obtained from Dr. Yung-san Liang, University of Massachusetts Lowell, Mass. as part of a sub-contract from National Institute of Allergy and Infectious Diseases (AI # 052590). Cercarial stages of the parasite were collected from these infected snails (suspended in warm distilled water) by exposing them to a bright light source for 1 hour. Emerged cercariae were than concentrated by passing through a wire mesh sieve (38 μm; Newark Wire Cloth Co., Newark, N.J.) and washed several times with phosphate buffered saline containing 10 μg/ml gentamicin. Cercariae suspended in phosphate buffered saline (at a concentration of 10,000 cercariae/ml) and were then transformed into schistosomulae by incubating then in linolenic acid coated culture flasks (coated with 2 mg/ml linoleic acid) for 30 min at 37° C. Following incubation, the transformed schistosomulae were separated from the tails and resuspended in sterile RPMI 1640 media containing 10 μg/ml gentamicin. ES products from the transformed schistosomulae were then collected by incubating the schistosomulae in a culture flask for 16–24 hrs at 37° C.

Following incubation, the culture supernatant containing the ES products were sterile filtered (0.2 μm, Costar, Cambridge, Mass.), concentrated up to 15-fold using a Centriprep concentrator (3000 dalton cut off; Amicon, Beverly, Mass.) and the proteins were separated in a 12–15% sodium dodecyl sulfate-polyacrylamide gel by electrophoresis (SDS-PAGE) under non-reducing conditions (Bio-Rad, Cambridge, Mass.). Molecular weight standards purchased from Sigma Chemicals (St. Louis, Mo.) were run simultaneously in the same gel to estimate the molecular mass of the proteins in the ES products. Following separation, the protein bands in the SDS-PAGE gel were stained with copper stain (Bio-Rad) and protein bands corresponding to 211, 155.8, 67.8, 53.6, 38.2, 28.5, 21.2 and 16.8 kDa were cut out using a sharp blade. The proteins were then electroeluted (Bio-Rad) from the gel slices, and dialyzed against sterile phosphate buffered saline. The eluted proteins were then tested for anti-inflammatory activity as described below. Purity of the 16.8 kDa protein preparation was tested by running in an SDS-PAGE gel. The 16.8 kDa is designated herein as Sm 16.8.

Isoelectric focusing and separation of the purified protein in a two-dimensional SDS-PAGE showed that Sm 16.8 contains only a single species of protein with a pI of 5.9. Treatment of Sm 16.8 with 2-mercaptoethanol (reducing conditions) had no effect on the size of the protein suggesting that there are no disulfide bonds in its structure. In addition Sm 16.8 has been shown to be trypsin sensitive.

EXAMPLE 2

Effects of Sm 16.8 on Cytokine Expression

In order to characterize the mechanisms by which ES products and particularly Sm 16.8 inhibits inflammation, approximately 5 μg of purified Sm 16.8 purified was added to human keratinocyte cultures (Clone C1, purchased from Clonetics Corporation, San Diego, Calif.) grown in 6 well plates ($1 \times 10^5$ cells/well) in keratinocyte growth medium KGM (Clonetics Corp., San Diego, Calif.). At different time intervals after the start of the culture (i.e. 4 hrs, 8 hrs, 16 hrs, 24 hrs, 48 hrs and 72 hrs) samples of cells and their supernatants were collected for measuring intracellular and secreted levels of the cytokines IL-1, IL-1, IL-1ra, IL-2, IL-6, IL-10, and IFN-γ by sandwich enzyme-linked immunosorbent assay (ELUSA), metabolic labelling and immunoprecipitation studies, Northern blot analysis or polymerase chain reaction (PCR). [See, e.g., Ramaswamy et al., *Parasite Immunology*, 16:435–445 (1994); and Ausubel et al., *Current Protocols in Molecular Biology*, eds. J. Wiley and Sons, (1997), both of which are incorporated herein by reference.] Cytokine values in cells and supernatants collected from control cultures that were grown simultaneously in media alone (i.e., not stimulated with the protein) was used as the baseline value.

Results of the assay show that treatment of the cells with Sm 16.8 resulted in 30–33 fold increase in secreted and intracellular levels of IL-1ra as measured by ELUSA. Metabolic labelling studies showed that the increased intracellular synthesis of IL-1ra occurred as early as 4 hrs after treatment with the protein. Northern blot analysis confirmed this finding by showing that message (mRNA) levels for IL-1ra increased in human keratinocytes within 4 hrs after treatment with the protein.

Analysis of intracellular and secreted levels of IL-1α and IL-1β in human keratinocytes cultures treated with Sm 16.8 at 5 µg/ml per $1 \times 10^5$ cells showed that these two pro-inflammatory cytokines are absent or are present only below the base line value. This finding was confirmed by both Northern blot analysis and metabolic labelling studies. Message (mRNA) levels for both IL-1α and IL-1β were absent in human keratinocytes 4 hrs after stimulation with the protein.

Thus, the parasite-derived protein Sm 16.8, suppressed IL-1α and IL-1β production in human keratinocytes within 4 hrs after exposure.

EXAMPLE 3

Effects of Sm 16.8 on Cytokine Production in Human Skin Organ Culture

Parasitic stages of the *S. mansoni* that secrete Sm 16.8 were applied to human skin organ cultures and cytokines released into the culture medium were analyzed. Skin was cultured according to the method of Buchshaun et al., *J. Cut. Path.*, 20:21–27 (1993) incorporated herein by reference. Approximately 3 cm³ neonatal normal human foreskin obtained from Swedish American Hospital, Rockford Ill. were exposed to 250 parasites (this translates to approximately 50 µg of the anti-inflammatory protein) and grown in air/liquid biphasic cultures containing RPMI 1640, 5% fetal bovine serum (FBS), 5% human AB serum (Sigma), 10 µg/ml gentamicin and 25 µg/ml fungizone (Gibco, Grand Island, N.Y.) at 37° C. and 5% $CO_2$. At the end of 72 hrs of culture, concentration of cytokines (IL-1, IL-1ra, IL-10 and IFN-γ) in the culture supernatant was measured as described above as were the concentrations in an epidermal cell lysate prepared from the culture. Epidermal cell lysates were prepared by freeze-thawing in liquid nitrogen and cell debris was removed by centrifugation.

Control skin samples grown in media without exposure to the parasite were used for obtaining baseline cytokine values.

Results of the ELISA assay indicate that exposure to the parasite resulted in 15–20 fold increase in secreted levels of IL-1ra and greater than 110-fold increase in epidermal cell lysate of human skin organ cultures.

The levels of IL-1α on the other hand was increased only by 0.5 to 1 fold over the base line. These data demonstrate that migration of schistosomes through human skin stimulate the production of substantial quantities of the anti-inflammatory cytokine IL-1ra, as predicted from the cell culture system.

EXAMPLE 4

Immunomodulatory Effects of Sm 16.8

Single cell suspension of spleen and axillary lymph node cells (lymphocytes) were prepared from what CD1 strain of mice (Charles River, Wilmington, MA) that were infected 10 weeks earlier with *S. mansoni* using methods well known in the art. See, e.g., Mosca et al., *Immunol. Lett.*, 15; 13(5):245–253 (1986) and Ramaswamy et al., *Parasite Immunol.*, 16:435–445 (1994). Cells were placed in RPMI 1640 medium containing 2 mM glutamine, 0.04% sodium bicarbonate (Sigma), 1 mM sodium pyruvate (Gibco), 25 mM HEPES (Sigma), 50 mM 2-mercaptoethanol and 10 µg/ml gentamicin.

During the process of proliferation, lymphocytes take up and incorporate thymidine. By incubating lymphocytes in media containing $^3$H-labelled thymidine for a definite period of time, and then measuring the amount of $^3$H-thymidine that is incorporated into the cells, it is possible to calculate the proportion of dividing cells in the cultures. Addition of ES products depleted of Sm 16.8 resulted in 1.8-fold increase in $^3$H-thymidine uptake by spleen cells and 9-fold increase in $^3$H-thymidine up take by axillary lymph node cells indicating that ES depleted of Sm 16.8 was capable of stimulating proliferation of lymphocytes from infected mice. Prior incubation of spleen and axillary lymph node cells with Sm 16.8 for before addition of the ES products depleted of Sm 16.8, resulted in near baseline values of $^3$H-thymidine up take by the cells indicating that Sm 16.8 is capable of suppressing antigen specific lymphoproliferation.

ES products were depleted of Sm 16.8 by running ES products on non-reducing gel SDS-PAGE gel as described in Example 1. The band corresponding to Sm 16.8 was excised and set aside. The remaining bands were electroeluted, pooled and dialyzed against PBS. The dialyzing membrane had a molecular weight cutoff of 3 kDa.

When IL-2 levels were measured (by ELISA) in the supernatants of spleen and axillary lymph node cell cultures that were set up as described above, a significant reduction in the ability of the lymphocytes to secrete IL-2 was observed in the presence of Sm 16.8. This suggests that the Sm 16.8 also has an immunomodulatory function.

EXAMPLE 5

Effects of Sm 16.8 LPS Induction of Il-1α

Based on its properties described in Examples 2 & 3, Sm 16.8 appears to specifically suppress the pro-inflammatory cytokine IL-1α in cutaneous cells. To test the extent to which Sm 16.8 can suppress IL-1α production in human keratinocytes, human keratinocytes were stimulated in vitro with lipopolysaccharide (LPS), a potent IL-1α inducing molecule, and tested the ability of Sm 16.8 to reverse or prevent the IL-1α inducing effect of LPS on human keratinocytes. In these studies a titration curve for LPS was plotted (0.00001–10 µg/ml) to identify the minimum concentration of LPS needed to induce maximum IL-1α secretion from keratinocytes. Tissue culture methods and cytokine analysis used in these experiments were as described in Example 2. These experiments showed that LPS at a concentration of 0.1 µg/ml or above had maximal effect on IL-1α production by human keratinocytes (19–21 ng of IL-1α per $1 \times 10^6$ cells). To test the modulatory effect of Sm 16.8 on IL-1α secretion in keratinocytes, we added Sm 16.8 in varying concentration (0.6125 to 20 µg/ml) simultaneously to LPS treated (1 mg/ml) human keratinocytes in vitro. The results showed a concentration dependent decrease in LPS induced IL-1α secretion by Sm 16.8 treated human keratinocytes. A concentration of 2.5 µg/ml of Sm 16.8 in the culture media was highly effective in suppressing LPS induced IL-1α secretion by human keratinocytes.

EXAMPLE 6

Effects of Sm 16.8 on Neutrophil Infiltration

IL-1 plays a major role in acute cutaneous inflammation. Since the preceding in vitro studies showed that Sm 16.8 can suppress LPS induced IL-1α in keratinocytes, Sm 16.8 was tested for its ability to suppress lymphocyte (neutrophil) infiltration (a hallmark of acute inflammation) in vivo in the skin. In these studies 50 μg of a 1 mg/ml suspension of LPS in PBS was injected subcutaneously into the skin of CD1 strain of mice (Charles River Laboratories, Wilmington, Mass.) to induce neutrophil infiltration. Preliminary titration experiments showed that this concentration of LPS induced maximum neutrophil infiltration into the skin of mice within 24 hrs. To determine the modulatory effect of Sm 16.8 on neutrophil infiltration, we added Sm 16.8 in varying concentrations (0.6125 to 20 μg/ml) to 1 mg/ml of LPS in PBS and injected subcutaneously into the skin of mice.

The number of neutrophils infiltrated in the skin 24 hrs after injection were counted after removing the treated area of the skin, fixing it in buffered formalin, processing the tissue in paraffin, cutting five μm serial sections of the entire skin piece and staining with hematoxylin/eosin. Neutrophils were identified morphologically in these sections and their total numbers (in 30–60 fields) were counted using a 3 mm$^2$ grid (100×). The values were then expressed as mean cell ±SD per 3 mm$^2$ area of skin. These studies showed that LPS induced significant neutrophil infiltration (51+3 per 3 mm$^2$) into the skin.

Sm 16.8 was shown to completely suppress the LPS induced neutrophil infiltration into the skin in a dose dependent manner. Maximum suppression was evident at a dose of 2.5 μg/ml and above. These data thus suggested that Sm 16.8 prevented neutrophil infiltration into the skin in an in vivo model.

EXAMPLE 7

Effects of Sm 16.8 on Expression of ICAM-1

Infiltration and entry of neutrophils from systemic circulation into the skin is facilitated by cytokine induced expression of intercellular adhesion molecules, for example ICAM-1, on the surface of endothelial cells. Besides the endothelial cells, keratinocytes, dermal dendritic cells and possibly other dermal cells may also express ICAM-1 in response to pro-inflammatory cytokines such as IL-1α. Since the foregoing Examples show that Sm 16.8 suppresses IL-1α expression and prevents neutrophil infiltration into the skin, studies were conducted to determine whether Sm 16.8 interferes with expression of ICAM-1 in the skin.

In vivo experiments were designed in CD1 mice similar to those described in Example 6. The mice were injected subcutaneously with same concentration of LPS (1 mg/ml) and varying concentrations of Sm 16.8 (0.6125 to 20 μg/ml). Skin samples from the injected sites were snap frozen in OCT compound (Miles Inc. Elkhart, Ind.) at −70° C. and were processed for cryostat sectioning. Sections of 7–8μ thickness were prepared on APES coated slides (Sigma, St. Louis, Mo.), fixed in acetone and used in an immunohistochemical assay to detect ICAM-1.

To detect ICAM-1 antigens in the skin, sections were incubated (for 60 min at room temperature) with biotinylated hamster anti-mouse CD54 antibodies (anti-ICAM-1 antibodies) (Pharminigen, San Diego, Calif.) after blocking with Superblock (Pierce Chemicals, Rockford, Ill.). Alkaline phosphatase labeled streptavidin (Pierce Chemicals) was used to detect the biotin associated with the primary antibody and the color was developed using Fast Red (Pierce Chemicals).

Endogenous alkaline phosphatase activity was blocked using a blocking buffer (Pierce Chemicals) for 15 min before the addition of Fast Red. Appropriate controls without the primary and secondary antibodies were processed simultaneously. These studies showed that ICAM-1 expression is significantly increased in the endothelial cells lining the capillaries of dermis and hypodermis, and on several epidermal and dermal cells after treatment with LPS. However, treatment with Sm 16.8 completely suppressed the LPS induced ICAM-1 expression in the skin in a dose dependent manner. Maximum ICAM-1 suppression was evident in mice treated with 10 μg/ml or more of Sm 16.8. Thus, these studies demonstrate that one of the mechanisms underlying the anti-inflammatory and immunomodulatory activities of Sm 16.8 is its ability to down regulate or to suppress ICAM-1 expression in the skin.

EXAMPLE 8

Therapeutic and Proph lactic Uses of Sm 16.8

The anti-inflammatory immunomodulatory properties of Sm 16.8 and related polypeptides described in detail above may be exploited in therapeutic methods for the treatment of diseases characterized by inflammatory process and with production of pro-inflammatory cytokines. Exemplary diseases include cutaneous diseases such as urticaria, atopic dermatitis, cutaneous allergic conditions such as contact sensitivity, and psoriasis. See, e.g., Cecil, *Textbook of Medicine*, Wyngaarden et al. eds., W. B. Sanders, Philadelphia, Pa. (1985).

Therapeutic applications of Sm 16.8 and Sm 16.8-related polypeptides are not limited to cutaneous diseases. Many other diseases (systemic) are associated with inflammatory processes and are amenable to treatment according to the present invention. Exemplary diseases include but are not limited to Hashimoto's Thyroiditis, inflammatory polyneuropathy, chronic granulomatous disease, rheumatoid arthritis and others.

Methods for treating diseases such as those exemplified above involve the administration of the polypeptides or antibodies of the present invention via an appropriate route of administration. For example, treatment of cutaneous diseases may be accomplished by the topical application of the polypeptides of the invention preferably in a suitable carrier such as pharmaceutically acceptable lotions, creams, salves or other vehicles or by subcutaneous, intradermal, or hypodermal injection in an appropriate vehicle. The carrier may also include excipients which facilitate the penetration of the 5 polypeptides into the skin. The determination of the appropriate dosages and dosage schedules for optimal therapeutic effect is readily determined using routine methods such as those described in the forgoing examples.

The polypeptides and pharmaceutical compositions of the present invention are also useful in treating systemic inflammatory diseases such as those described above. In such methods, the polypeptides or pharmaceutical compositions of the present invention may be administered via intravenous, intramuscular, subcutaneous, oral or other routes of administration. Therapeutically effective doses are readily determined by methods well known in the art.

Polypeptides according to the present invention are also useful for producing vaccines for immunoprophylaxis of schistosomiasis. Useful vaccines induce the production of antibodies directed to one or more epitopes of Sm 16.8 and serve to neutralize the anti-inflammatory effects of the protein, thereby allowing the host to mount an effective immune response against the invading parasite. Vaccines comprise one or more polypeptides according to the present invention and optionally, a suitable diluent, adjuvant or carrier.

The foregoing Examples are presented by way of illustration and are not intended to in any way limit the scope of the present invention as set out in the appended claims. All references set out herein are incorporated by reference.

We claim:

1. An isolated purified anti-inflammatory polypeptide obtained from *Schistosoma mansoni* wherein said polypeptide has a molecular weight of 16.8kDa on a non-reducing SDS-polyacrylamide gel and said polypeptide has an isoelectric point of 5.9.

2. A method for suppressing inflammation, the method comprising administering to a subject an effective dose of the polypeptide of claim 1.

* * * * *

UNITED STATES PATENT AND TRADEMARK OFFICE
CERTIFICATE OF CORRECTION

PATENT NO.    : 6,372,219 B1
DATED         : April 16, 2002
INVENTOR(S)   : Salafsky et al.

It is certified that error appears in the above-identified patent and that said Letters Patent is hereby corrected as shown below:

Title page,
Item [76], Inventors, replace "Ramaswamy Kalyanasundaram", with
-- Kalyanasundaram Ramaswamy --.

Column 2,
Line 50, replace "imflammatory, response" with -- imflammatory response --.
Line 58, replace "dernatitis" with -- dermatitis --.

Column 3,
Line 12, replace "IL-1αand" with -- IL-1α and --.

Column 5,
Line 58, replace "Biomphalaia" with -- Biomphalaria --.

Column 6,
Line 56, replace "(ELUSA)" with -- (ELISA) --.

Column 7,
Line 1, replace "ELUSA" with -- ELISA --.
Line 63, replace "what CD1 strain" with -- wht CD1 strain --.

Column 8,
Line 18, "Sm 16.8 for before" with -- Sm 16.8 for 6 hours before --.
Lines 23-28, please move to column 8, line 16, after "mice." -- ES products were depleted of Sm 16.8 by running ES products on non-reducing gel SDS-PAGE gel as described in Example 1. The band corresponding to Sm 16.8 was excised and set aside. The remaining bands were electroeluted, pooled and dialyzed against PBS. The dialyzing membrane had a molecular weight cutoff of 3 kDa. --

Column 9,
Line 23, replace "51+3 per 3 mm$^2$)" with -- 51±3 per 3 mm$^2$ --.

Column 10,
Line 16, replace "Proph lactic" with -- Prophylactic --.
Line 23, replace "derrnatitis" with -- dermatitis --
Line 46, replace "the 5 polypeptides" with -- the polypeptides --.

UNITED STATES PATENT AND TRADEMARK OFFICE
CERTIFICATE OF CORRECTION

PATENT NO. : 6,372,219 B1
DATED : April 16, 2002
INVENTOR(S) : Salafsky et al.

It is certified that error appears in the above-identified patent and that said Letters Patent is hereby corrected as shown below:

Column 21,
Line 8, replace "proinflammatory" with -- pro-inflammatory --.

Signed and Sealed this

Nineteenth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,372,219 B1 Page 1 of 1
APPLICATION NO. : 09/180446
DATED : April 16, 2002
INVENTOR(S) : Salafsky et al.

It is certified that error appears in the above-identified patent and that said Letters Patent is hereby corrected as shown below:

On title page (73)
Under Assignee Information, please add:

The Board of Trustees of the University of Illinois
Urbana, Illinois

Signed and Sealed this

Seventeenth Day of July, 2007

JON W. DUDAS
*Director of the United States Patent and Trademark Office*